(12) United States Patent
Fleming

(10) Patent No.: US 9,978,140 B2
(45) Date of Patent: May 22, 2018

(54) RETINAL IMAGE PROCESSING

(71) Applicant: Optos PLC, Dunfermline, Fife, Scotland (GB)

(72) Inventor: Alan Duncan Fleming, Edinburgh (GB)

(73) Assignee: OPTOS PLC, Dunfermline, Fife (GB)

( * ) Notice: Subject to any disclaimer, the term of this patent is extended or adjusted under 35 U.S.C. 154(b) by 144 days.

(21) Appl. No.: 15/139,179

(22) Filed: Apr. 26, 2016

(65) Prior Publication Data

US 2017/0309014 A1    Oct. 26, 2017

(51) Int. Cl.
*G06K 9/00* (2006.01)
*G06T 7/00* (2017.01)
(Continued)

(52) U.S. Cl.
CPC .......... *G06T 7/0012* (2013.01); *A61B 3/0025* (2013.01); *A61B 3/12* (2013.01);
(Continued)

(58) Field of Classification Search
CPC  G06T 7/0012; G06T 7/73; G06T 7/70; G06T 5/002; G06T 2207/10101;
(Continued)

(56) References Cited

U.S. PATENT DOCUMENTS 3,944,341 A    3/1976 Pomerantzeff
4,213,678 A    7/1980 Pomerantzeff et al.
(Continued)

FOREIGN PATENT DOCUMENTS

CN    101489468 A    7/2009
CN    101534701 A    9/2009
(Continued)

OTHER PUBLICATIONS

Fleming, A.D., et al., "Automatic Detection of Retinal Anatomy to assist Diabetic Retinopathy Screening", Phys. Med. Biol. 52, pp. 331-345 (Dec. 21, 2006).
(Continued)

*Primary Examiner* — Van D Huynh
(74) *Attorney, Agent, or Firm* — Foley & Lardner LLP; Pavan Agarwal; Shabbi S. Khan

(57) ABSTRACT

The present disclosure relates to a computer-readable storage medium storing instructions that can cause a processor to process image data defining an image of a vascular structure of temporal vascular arcades of a retina to estimate a location of the fovea of the retina in the image by transforming received image data such that the vascular structure in the image defined by the transformed image data is more circular than the vascular structure defined by the image data; calculating, for each of a plurality of pixels of the transformed image data, a respective local orientation vector indicative of the orientation of any blood vessel present in the image; calculating a normalized local orientation vector for each of the pixels; operating on an array of accumulators; and estimating the location of the fovea in the image of the retina using the location of a pixel of the transformed image data.

24 Claims, 8 Drawing Sheets

(51) Int. Cl.
*A61B 3/00* (2006.01)
*A61B 3/12* (2006.01)
*G06T 7/73* (2017.01)

(52) U.S. Cl.
CPC ............ *G06T 7/004* (2013.01); *G06T 7/0081* (2013.01); *G06T 7/73* (2017.01); *G06T 2207/20061* (2013.01); *G06T 2207/30041* (2013.01); *G06T 2207/30101* (2013.01)

(58) Field of Classification Search
CPC . G06T 2207/30041; G06T 2207/30101; A61B 3/0025; A61B 3/12
USPC .......................................................... 382/128
See application file for complete search history.

(56) References Cited

U.S. PATENT DOCUMENTS

| | | |
|---|---|---|
| 4,365,874 A | 12/1982 | Milburn et al. |
| 4,666,269 A | 5/1987 | Nakamura et al. |
| 4,699,482 A | 10/1987 | Utsugi |
| 4,772,114 A | 9/1988 | Fukui et al. |
| 5,585,873 A | 12/1996 | Shalon et al. |
| 5,815,242 A | 9/1998 | Anderson et al. |
| 5,835,190 A | 11/1998 | Miyake |
| 5,975,697 A | 11/1999 | Podoleanu et al. |
| 6,081,304 A | 6/2000 | Kuriyama et al. |
| 6,160,826 A | 12/2000 | Swanson et al. |
| 6,288,784 B1 | 9/2001 | Hitzenberger et al. |
| 6,337,920 B1 | 1/2002 | Muhlhoff |
| 6,409,346 B1 | 6/2002 | Koest et al. |
| 6,690,516 B2 | 2/2004 | Aritake et al. |
| 6,996,260 B1 * | 2/2006 | Skands ................ A61B 3/12 382/117 |
| 7,068,444 B2 | 6/2006 | Nishi |
| 7,134,754 B2 | 11/2006 | Kerr et al. |
| 7,224,507 B2 | 5/2007 | Kamiya et al. |
| 7,275,826 B2 | 10/2007 | Liang |
| 7,637,617 B2 | 12/2009 | Liu et al. |
| 7,909,465 B2 | 3/2011 | Ho et al. |
| 7,959,290 B2 | 6/2011 | Cairns et al. |
| 8,422,750 B2 | 4/2013 | Atkinson et al. |
| 8,811,745 B2 * | 8/2014 | Farsiu .................. A61B 5/0066 382/128 |
| 2002/0101568 A1 | 8/2002 | Eberl et al. |
| 2002/0151774 A1 | 10/2002 | Soller et al. |
| 2002/0159621 A1 | 10/2002 | Callies et al. |
| 2003/0103249 A1 | 6/2003 | Hartmann et al. |
| 2003/0156416 A1 | 8/2003 | Stopa et al. |
| 2004/0135971 A1 | 7/2004 | Ulbers |
| 2005/0122575 A1 | 6/2005 | Pentico et al. |
| 2006/0072215 A1 | 4/2006 | Nishi |
| 2006/0187462 A1 | 8/2006 | Srinivasan et al. |
| 2007/0010313 A1 | 1/2007 | Akita |
| 2007/0024965 A1 | 2/2007 | Sander |
| 2007/0030449 A1 | 2/2007 | Liang |
| 2007/0046948 A1 | 3/2007 | Podoleanu et al. |
| 2007/0109619 A1 | 5/2007 | Eberl et al. |
| 2007/0285793 A1 | 12/2007 | Liu et al. |
| 2007/0291277 A1 | 12/2007 | Everett et al. |
| 2008/0151185 A1 | 6/2008 | Saito et al. |
| 2009/0009715 A1 | 1/2009 | Mensink |
| 2009/0093798 A1 | 4/2009 | Charles |
| 2009/0268162 A1 * | 10/2009 | Stetson .................. A61B 3/102 351/246 |
| 2010/0141895 A1 | 6/2010 | Cairns et al. |
| 2010/0142767 A1 * | 6/2010 | Fleming ............... G06K 9/0061 382/117 |
| 2010/0149073 A1 | 6/2010 | Chaum et al. |
| 2010/0328606 A1 | 12/2010 | Peyman |
| 2011/0234978 A1 | 9/2011 | Hammer et al. |
| 2012/0027275 A1 * | 2/2012 | Fleming ................. G16H 50/20 382/128 |
| 2012/0133888 A1 | 5/2012 | Gray et al. |
| 2012/0195481 A1 | 8/2012 | Gonzalez Penedo et al. |
| 2014/0185904 A1 * | 7/2014 | Yonezawa .......... G06K 9/00604 382/133 |
| 2017/0202453 A1 * | 7/2017 | Sekiguchi ............... G06T 7/564 |

FOREIGN PATENT DOCUMENTS

| | | |
|---|---|---|
| DE | 20 2008 013 344 U1 | 1/2009 |
| EP | 0 245 21 A1 | 3/1981 |
| EP | 0 698 991 A2 | 2/1996 |
| EP | 0 730 428 A1 | 9/1996 |
| EP | 1 933 187 A1 | 6/2008 |
| EP | 2 040 606 B1 | 4/2009 |
| EP | 2 064 988 A1 | 6/2009 |
| EP | 2 465 413 A1 | 6/2012 |
| GB | 1 454 675 A | 11/1976 |
| GB | 2 440 163 A | 1/2008 |
| JP | S54-033392 A | 3/1979 |
| JP | S59-006029 A | 7/1982 |
| JP | S61-052850 A | 3/1986 |
| JP | S62-008730 A | 1/1987 |
| JP | S62-031941 A | 7/1987 |
| JP | H01-265936 A | 10/1989 |
| JP | H03-198039 A | 8/1991 |
| JP | H03-227168 A | 10/1991 |
| JP | H04-505061 A | 9/1992 |
| JP | H05-309072 A | 11/1993 |
| JP | H06-148525 A | 5/1994 |
| JP | H06-261862 A | 9/1994 |
| JP | H09-197280 A | 7/1997 |
| JP | 3490088 B2 | 9/1997 |
| JP | H09-509337 A | 9/1997 |
| JP | H11-123178 A | 5/1999 |
| JP | H11-223747 A | 8/1999 |
| JP | 2001-290102 A | 10/2001 |
| JP | 2002-098901 A | 4/2002 |
| JP | 2002-515593 A | 5/2002 |
| JP | 2005-500870 A | 1/2005 |
| JP | 2005-507727 A | 3/2005 |
| JP | 2005-189825 A | 7/2005 |
| JP | 2005-326220 A | 11/2005 |
| JP | 2006-230799 A | 9/2006 |
| JP | 2009-119153 A | 6/2009 |
| JP | 2009-119173 A | 6/2009 |
| JP | 4287375 B2 | 7/2009 |
| JP | 2009-543585 A | 12/2009 |
| JP | 2010-508932 A | 3/2010 |
| JP | 2011-512916 A | 4/2011 |
| JP | 50-020587 A | 9/2012 |
| JP | 2012-525184 A | 10/2012 |
| WO | WO-92/19930 A1 | 11/1992 |
| WO | WO-95/13012 A2 | 5/1995 |
| WO | WO-99/20174 A1 | 4/1999 |
| WO | WO-99/27844 A1 | 6/1999 |
| WO | WO-02/058590 A2 | 8/2002 |
| WO | WO-2008/009877 A1 | 1/2008 |
| WO | WO-2008/056110 A2 | 5/2008 |
| WO | WO-2008/116270 A1 | 10/2008 |
| WO | WO-2009/029604 A2 | 3/2009 |
| WO | WO-2009/084842 A2 | 7/2009 |
| WO | WO-2010/125394 A1 | 11/2010 |
| WO | WO-2011/121962 A1 | 10/2011 |
| WO | WO-2011/135348 A2 | 11/2011 |

OTHER PUBLICATIONS

Gonzalez, R. C. and Woods, R. E.; "Chapter 3: Image Enhancement in the Spatial Domain, Section 3.6: Smoothing Spatial Filters", in Digital Image Processing, Pearson, 2007, pp. 119-123 and 134-137.

Niemeijer, M., et al., "Fast Detection of the Optic Disc and Fovea in Color Fundus Photographs", Medical Image Anal. 13(6):859-70 (Dec. 2009), 25 pages.

Schalkoff, R. J., "Image Grey-Level Modeling and Early Processing Fundamentals, Parts I and II" in Digital Image Processing and Computer Vision, John Wiley & Sons, 1992, pp. 89-94 and 146-152.

Soares, J., et al., Retinal vessel segmentation using the 2-D Gabor wavelet and supervised classification, IEEE Transactions on Medical Imaging, vol. 25, Issue 9, pp. 1214-1222 (IEEE, Sep. 2006).

(56) References Cited

OTHER PUBLICATIONS

Soares, Joao V.B., and Cesar, Jr., Roberto M.; "Chapter 8: Segmentation of Retinal Vasculature Using Wavelets and Supervised Classification: Theory and Implementation" in Automated Image Detection of Retinal Pathology. CRC Press: 2009. pp. 221-261.
Fleming, Alan D., "Automatic Detection of Retinal Anatomy to Assist Diabetic Retinopathy Screening", published in Physics in Medicine and Biology vol. 52, No. 2, pp. 331-345 (IOP Publishing, Bristol, GB.
International Search Report for Application No. PCT/EP2017/059647 dated Jul. 11, 2017, 14 pages.
Shapiro, Linda G., "Computer Vision" Chapter 10 titled "Image Segmentation", Mar. 2000.
Abramoff et al., "Retinal Imaging and Image Analysis," IEEE Reviews in Biomedical Engineering, vol. 3, Jan. 2010, pp. 169-208.
Can et al., "A Feature-Based, Robust, Hierarchical Algorithm for Registering Pairs of Images of the Curved Human Retina," IEEE Transactions on Pattern Analysis and Machine Intelligence, vol. 24, No. 3, Mar. 2002, pp. 347-364.
Chinese Examination Report Application No. 201300476859 dated Jan. 21, 2016 and Summary of Chinese Examination Report (English Translation), 16 pages.
English Translation of Decision to Grant a Patent issued in corresponding Japanese application No. 2013-517526 dated Nov. 10, 2015.
English Translation of Decision to Grant Japanese Patent issued in corresponding application No. 2012-524285 dated Oct. 21, 2014.
English Translation of Decision to Grant Japanese Patent issued in corresponding application No. 2013517524 dated Mar. 15, 2016.
English Translation of Final Notification of Reasons for Refusal issued in corresponding Japanese application No. 2013-517526 dated Sep. 29, 2015.
English Translation of First Chinese Office Action issued in corresponding application No. 201080035688.7 dated Dec. 26, 2013.
English Translation of First Chinese Office Action issued in corresponding application No. 201180032861.2 dated Jul. 30, 2014.
English Translation of First Chinese Office Action issued in corresponding application No. 201180032916 dated Aug. 26, 2014.
English Translation of Japanese Decision to Grant a Patent issued in corresponding application No. 2013-517525 dated Mar. 29, 2016.
English Translation of Japanese Notification of Reasons for Refusal issued in corresponding application No. 2013517524 dated May 26, 2015.
English Translation of Japanese Notification of Reasons for Refusal issued in corresponding application No. 2013-517525 dated Jun. 30, 2015.
English Translation of Notification of Reasons for Refusal issued in corresponding Japanese application No. 2013-517526 dated Jun. 2, 2015.
English Translation of Second Chinese Office Action issued in application No. 20118064856 dated May 28, 2015.
English Translation of Second Chinese Office Action issued in corresponding application No. 201080035688.7 dated Jul. 30, 2014.
English Translation of Second Chinese Office Action issued in corresponding application No. 201180032861.2 dated Jan. 19, 2016.
English Translation of Second Chinese Office Action issued in corresponding application No. 201180032861.2 dated May 18, 2015.
English Translation of Second Chinese Office Action issued in corresponding application No. 201180032916 dated Jun. 1, 2015.
English translation of the First Chinese Office Action dated Nov. 18, 2014 for Chinese Patent Appln. No. 201180064856.
English Translation of the Second Chinese Office Action dated May 28, 2015 in connection with Chinese Patent Appln. No. 201180064856.
English Translation of the Third Chinese Office Action dated Feb. 3, 2016 in connection with Chinese Patent Appln. No. 201180064856.
English Translation of Third Chinese Office Action issued in corresponding application No. 201180032916 dated Feb. 15, 2016.
European Office Action dated Aug. 6, 2015 in European Patent Application No. 11808912.7.
Final Office Action in U.S. Appl. No. 15/001,676 dated Sep. 6, 2016.
Final Rejection issued in U.S. Appl. No. 13/805,595 dated Apr. 7, 2015.
Final Rejection issued in U.S. Appl. No. 13/805,595 dated Jun. 10, 2016.
Final Rejection issued in U.S. Appl. No. 13/805,599 dated Jun. 2, 2015.
Final Rejection issued in U.S. Appl. No. 13/805,599 dated Jul. 27, 2016.
Final Rejection issued in U.S. Appl. No. 13/805,604 dated Mar. 4, 2015.
Hu et al., "Multimodal Retinal Vessel Segmentation From Spectral-Domain Optical Coherence Tomography and Fundus Photography," IEEE Transactions on Medical Imaging, vol. 31, No. 10, Oct. 2012, pp. 1900-1911.
International Preliminary Report on Patentability dated Jul. 16, 2013 in PCT Application No. PCT/GB2011/52458.
International Search Report issued in application No. PCT/GB2010/051247 dated Nov. 17, 2010.
International Search Report issued in application No. PCT/GB2011/051037 dated Dec. 28, 2011.
International Search Report issued in application No. PCT/GB2011/051039 dated Sep. 29, 2011.
International Search Report issued in application No. PCT/GB2013/052556 dated Feb. 18, 2014.
International Search Report issued in PCT/GB2011/051038 dated Sep. 20, 2011.
International Search Report issued in PCT/GB2014/050480 dated May 22, 2014.
International Search Report dated Mar. 19, 2012 in PCT Application No. PCT/GB2011/52458.
Notification of Reasons for Refusal issued in Japanese application No. 2013548882 dated Oct. 27, 2015 with English Translation.
Notification of Reasons for Refusal with English Translation issued in Japanese application No. 2013548882 dated May 17, 2016.
Li et al., "A Multiscale Approach to Retinal Vessel Segmentation Using Gabor Filters and Scale Multiplication", 2006 IEEE Conferences on Systems, Man, and Cybernetics, Oct. 2006, pp. 3521-3527.
Non-Final Rejection in U.S. Appl. No. 15/001,676 dated Apr. 20, 2016.
Non-Final Rejection issued in U.S. Appl. No. 13/805,599 dated Jan. 26, 2015.
Non-Final Rejection issued in U.S. Appl. No. 13/389,060 dated Jan. 30, 2015.
Non-Final Rejection issued in U.S. Appl. No. 13/805,595 dated Dec. 10, 2015.
Non-Final Rejection issued in U.S. Appl. No. 13/805,595 dated Sep. 12, 2014.
Non-Final Rejection issued in U.S. Appl. No. 13/805,599 dated Mar. 3, 2016.
Non-Final Rejection issued in U.S. Appl. No. 13/805,604 dated Nov. 12, 2015.
Notice of Allowance issued in U.S. Appl. No. 13/389,060 dated Oct. 22, 2015.
Notification of Reasons for Refusal issued in corresponding Japanese application No. 20120524285 dated Jan. 28, 2014.
Office Action on U.S. Appl. No. 14/422,671 dated Jul. 29, 2016.
Non-Final Office Action issued in U.S. Appl. No. 15/013,545 dated Oct. 7, 2016.
Non-Final Office Action issued in U.S. Appl. No. 15/013,504 dated Oct. 6, 2016.
Final Office Action issued in U.S. Appl. No. 13/805,604 dated Jun. 27, 2016.
Notice of Allowance issued in U.S. Appl. No. 14/654,249 dated May 24, 2016.
International Search Report for Application No. PCT/EP2017/059648 dated Jul. 4, 2017, 16 pages.
Shapiro, L., et al, "Computer Vision", Mar. 2000,pp. 1-52.

\* cited by examiner

RETINAL IMAGE PROCESSING

TECHNICAL FIELD

The present disclosure generally relates to the field of medical image processing and, more particularly, to the processing of a retinal image to estimate the location of the fovea of the retina within the image.

BACKGROUND

Many eye diseases can be detected and diagnosed by imaging the retina. In a busy clinic it is not always possible to record even basic information such as whether the image is of the left or right eye. Automated analysis and manipulation of retinal images is a growing field. Automated analysis by computerised algorithms can provide assistance to clinicians in the form of disease detection or improved presentation modes.

SUMMARY

Many automated methods require positional information of the basic anatomical landmarks to aid their operation. This positional information may be input into software which may, for example: (i) project a retinal image into a uniform format which allows accurate dimensional measurements of the retina to be made; (ii) analyse multiple retinal field-of-view image sets, for example to identify fields-of-view and confirm that at all required fields-of-view are present; (iii) register multiple retinal images so that the location of disease visible in one modality can be identified in another; (iv) montage multiple retinal images to present clinicians with a wider view of the retina in one image; (v) present the user with a fly-through presentation of the retina; and/or (vi) perform automated disease determination; this can be so that the software operates only on the relevant area (for example, the optic disc in glaucoma, the macula in age-related macular degeneration) or so that the software ignores irrelevant areas (for example, the optic disc in diabetic retinopathy).

Although methods have been developed for determining the locations of anatomical features of the retina such as the optic disc and fovea in fundus reflectance photographs (mainly red and green light), the technical problem of automatically and reliably estimating the location of the fovea in a retinal images of other modalities, and for ultra-wide field views, presents a difficult challenge, owing to artefacts and pathology, variations in eye position and variations between image modalities.

In view of the shortcomings of conventional retinal image-processing methods and devices summarised above, the present disclosure relates to a non-transitory computer-readable storage medium storing computer program instructions which, when executed by a processor, cause the processor to process image data defining an image of a vascular structure of temporal vascular arcades of a retina to estimate a location of the fovea of the retina in the image by: receiving the image data; transforming the received image data such that the vascular structure in the image defined by the transformed image data is more circular than the vascular structure in the image defined by the received image data; calculating, for each of a plurality of pixels of the transformed image data, a respective local orientation vector indicative of the orientation of any blood vessel present in the image at or adjacent to the pixel; calculating a normalised local orientation vector for each of the plurality of pixels by normalising the local orientation vector calculated for each of the pixels so that the magnitude of the normalised local orientation vector at each of the pixels takes a common predetermined value; operating on an array of accumulators, wherein each accumulator in the array is associated with a respective pixel of the transformed image, by (i) for each of the plurality of pixels, adding a respective value to an accumulator associated with a pixel of the transformed image data that is offset from the pixel of the plurality of pixels by the predetermined value in a predetermined direction relative to the direction of the local orientation vector at the pixel of the plurality of pixels, and (ii) smoothing the values in the accumulators; and estimating the location of the fovea in the image of the retina using the location of a pixel of the transformed image data which is associated with an accumulator having accumulated an accumulated value which is within a predetermined range of an extremum of the accumulated values in the accumulators.

The present disclosure further relates to an image-processing apparatus comprising a processor and a memory, the memory storing instructions executable by the processor whereby the processor is operative to process image data defining an image of a vascular structure of temporal vascular arcades of a retina to estimate a location of the fovea of the retina in the image by: receiving the image data; transforming the received image data such that the vascular structure in the image defined by the transformed image data is more circular than the vascular structure in the image defined by the received image data; calculating, for each of a plurality of pixels of the transformed image data, a respective local orientation vector indicative of the orientation of any blood vessel present in the image at or adjacent to the pixel; calculating a normalised local orientation vector for each of the plurality of pixels by normalising the local orientation vector calculated for each of the pixels so that the magnitude of the normalised local orientation vector at each of the pixels takes a common predetermined value; operating on an array of accumulators, wherein each accumulator in the array is associated with a respective pixel of the transformed image data, by (i) for each of the plurality of pixels, adding a respective value to an accumulator associated with a pixel of the transformed image data that is offset from the pixel of the plurality of pixels by the predetermined value in a predetermined direction relative to the direction of the local orientation vector at the pixel of the plurality of pixels, and (ii) smoothing the values in the accumulators; and estimating the location of the fovea in the image of the retina using the location of a pixel of the transformed image data which is associated with an accumulator having accumulated an accumulated value which is within a predetermined range of an extremum of the accumulated values in the accumulators.

BRIEF DESCRIPTION OF THE DRAWINGS

Embodiments of the present disclosure will now be explained in detail, by way of example only, with reference to the accompanying figures, in which.

DETAILED DESCRIPTION OF EMBODIMENTS

Embodiment 1

Figure 1:
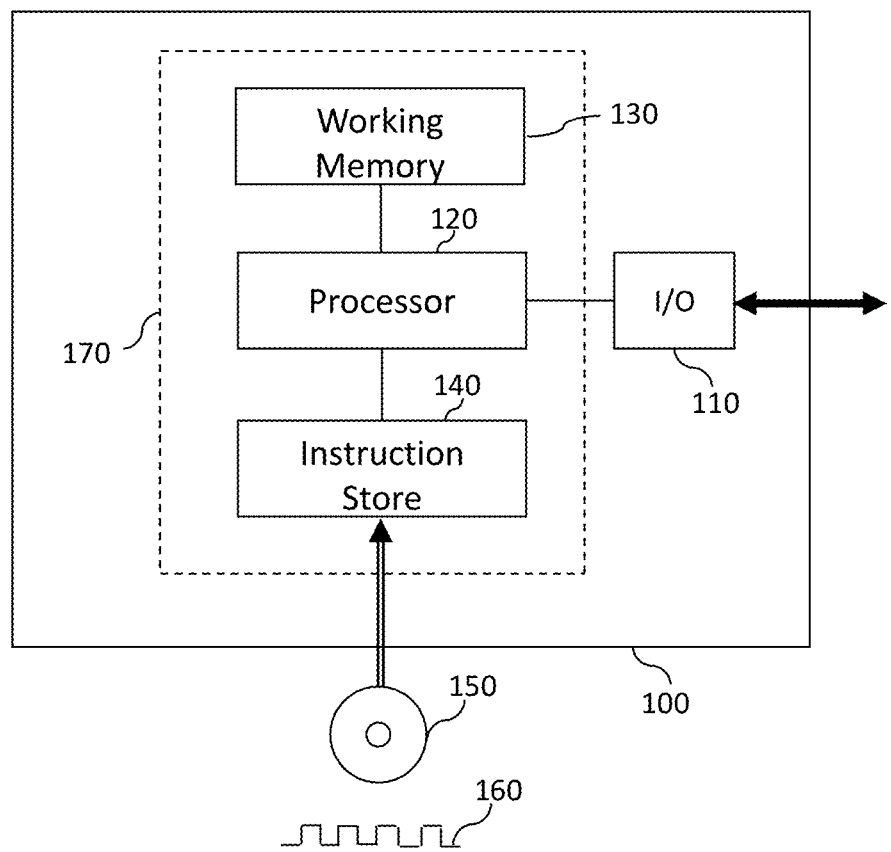
FIG. 1 is a schematic illustration of an image-processing apparatus according to embodiments of the present disclosure.

FIG. 1 illustrates an image-processing apparatus according to a first embodiment, which is configured to process image data defining an image of a vascular structure of the temporal vascular arcades of a retina to estimate a location of the fovea of the retina in the image. The two temporal vascular arcades (namely, the superior and inferior temporal vascular arcades, each comprising a vein and an artery) found in the retina of the eye define a vascular structure which follows a generally elliptical path as the blood vessels branch out from the optic disc, with the macula of the eye being surrounded by this elliptical path, and the center of the macula (namely, the fovea) being located approximately at the centre of the ellipse. The image-processing apparatus of the present embodiment exploits the geometry of this vascular structure in retinal images, using it to estimate the location of the fovea, by determining the location of a pixel which is indicative of the location of the fovea.

The image-processing apparatus of the present embodiment forms part of a programmable signal processing apparatus, as illustrated schematically in FIG. 1. The signal processing apparatus 100 shown in FIG. 1 comprises an input/output (I/O) section 110 for receiving image data defining an image of the retina, and for outputting the determined location of the pixel which is indicative of the location of the fovea, or a result of further processing operations based thereon, for example: (i) a more refined estimate of where the fovea is likely to be (which may correspond to the location of a pixel that is separated from the aforementioned pixel by a predetermined displacement vector); (ii) a determination of whether the image is of the right eye or the left eye; and/or (iii) an estimate of where the macula lies in the image. The determination of whether the image is of the right eye or the left eye may be determined by comparing the determined location of the pixel which is indicative of the location of the fovea with, for example, the center of the image, with a determined location of the optic disc, or with the location of a prominent darkening in the image, using techniques known to those skilled in the art.

The signal processing apparatus 100 further comprises a processor 120, a working memory 130 and an instruction store 140 storing computer-readable instructions which, when executed by the processor 120, cause the processor 120 to perform the processing operations hereinafter described to determine the location of the fovea in the retinal image. The I/O section 110, the working memory 130 and the instruction store 140 are communicably connected to the processor 120, as shown in FIG. 1. The instruction store 140 may comprise a ROM which is pre-loaded with the computer-readable instructions. Alternatively, the instruction store 140 may comprise a RAM or similar type of memory, and the computer-readable instructions can be input thereto from a computer program product, such as a computer-readable storage medium 150 such as a CD-ROM, etc. or a computer-readable signal 160 carrying the computer-readable instructions. The signal processing apparatus 100 may, for example, form part of a personal computer (PC) or a network server, and may comprise other components that are well-known (e.g. display, input device(s), etc.). In the present embodiment, the combination 170 of the hardware components shown in FIG. 1, comprising the processor 120, the working memory 130 and the instruction store 140, is configured to implement the functionality of the image-processing apparatus of the present embodiment, which will now be described in detail with reference to FIGS. 2 to 6.

Figure 2:
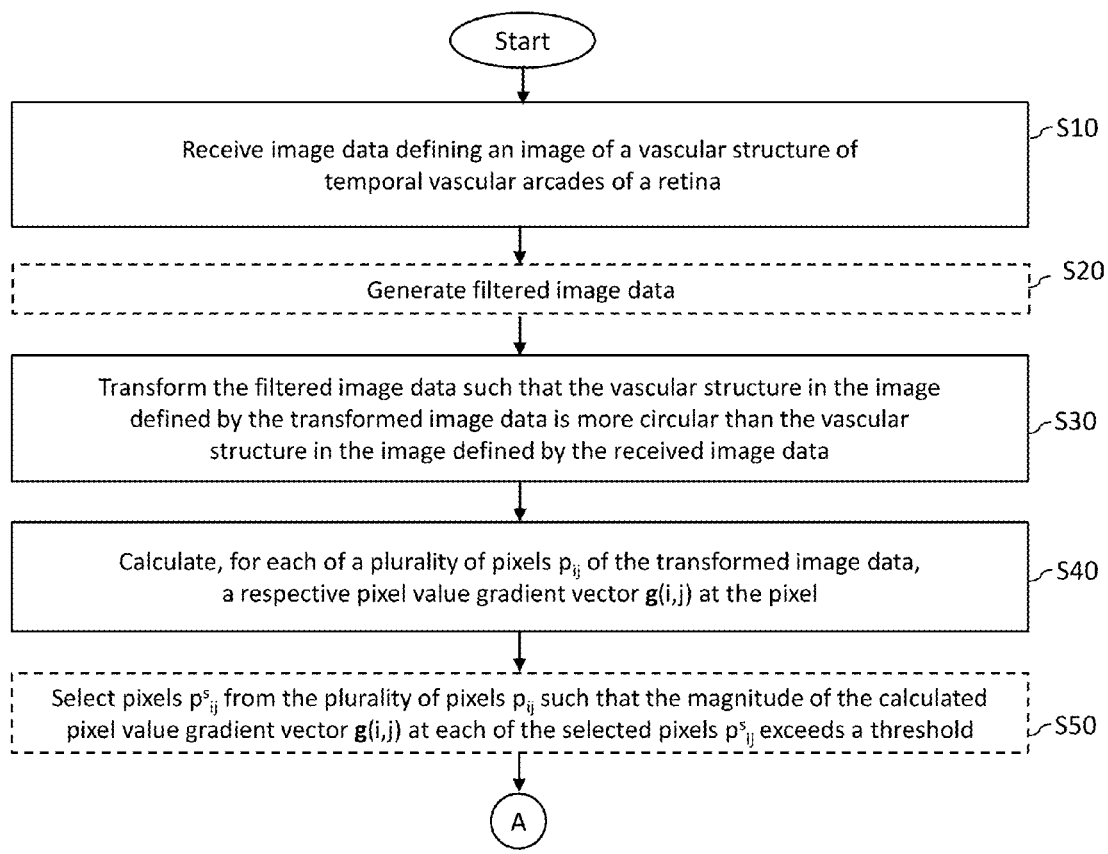
FIG. 2 is a first part of a flow diagram illustrating a process by which the image-processing apparatus of the first embodiment processes image data defining an image of a vascular structure of temporal vascular arcades of a retina to estimate a location of the fovea in the image.

FIG. 2 is a flow chart illustrating a first part of a process by which the image-processing apparatus 170 processes image data defining an image of a vascular structure of temporal vascular arcades of a retina to estimate a location of the fovea of the retina, which may be useful in a variety of different applications.

Firstly, in step S10, the processor 120 receives image data defining an image of a vascular structure of temporal vascular arcades of a retina via the I/O section 110. The acquired image data may define an retinal image which may be one of a number of different types that are known to those skilled in the art, for example a red and green (RG) reflectance image, an autofluorescence (AF) image, a fluorescein angiogram (FA) image, a reflectance scanning laser ophthalmoscope (SLO) image of the retina, or a colour fundus photograph of the retina, and may provide an ultra-wide-field view of the retina.

The processor 120 may then proceed to generate filtered image data in an optional step S20, wherein the processor 120 may pre-process the received retinal image data to enhance the vasculature in the image, using techniques known to those skilled in the art, for example as described in chapter 8 of the book "Automated Image Detection of Retinal Pathology" by H. Jelinek and M. J. Cree (CRC Press, Jan. 1, 2009). For example, the complex-valued Gabor kernel $$g(x, y; \lambda, \theta, \psi, \sigma, \gamma) = \exp\left(-\frac{x'^2 + \gamma^2 y'^2}{2\sigma^2}\right)\exp\left(i\left(2\pi\frac{x'}{\lambda} + \psi\right)\right)$$

may be used to generate convolved images, with the value of $\theta$ taking each value $2a\pi/N$ for $a=0 \ldots N-1$, where N is the number of orientations used in the evaluation which, may, for example, be between 8 and 12 (although reducing N to 6 in the pre-processing of RG images was not found to be detrimental). Values used for the other parameters in the Gabor kernel g may, for example, be:

$$\sigma=2.75\sqrt{s},\ \gamma=0.37,\ \lambda=7s,\ \psi=0.$$

The parameter s sets the scale. The value of s=2 was found to be well-suited for the pre-processing of Optomap™ images. However, the ideal value of s depends on the magnification of the image (or the real dimension in microns per pixel) and this is variable between imaging modalities and image formats. Also, a range of values of s may be used to account for vessels with a range of diameters. In this case, the resulting vessel enhancements at each value of s may be combined, for example, by pixel-by-pixel addition.

In this example, an array of complex-valued images is generated by convolution of the image by each Gabor kernel. Each element of this array is generated with one of the kernels:

$$U(a) = -\log\left(\lambda, \frac{a\pi}{N}, \psi, \sigma, \gamma\right)$$

At each pixel, the orientation index is found which gave the maximum absolute response:

$$A(x, y) = \arg \max_{a=0\ldots N-1} |U(x, y; a)|$$

This is the locally dominant (discretised) angle for pixels on a vessel, i.e. the orientation of the vessel.

The complex vessel-enhanced image, V, in which blood vessels appear brighter than the background, has a value at each pixel which is selected from one of the images in array U:

$$V(x,y)=U(x,y;A(x,y)), \forall (x,y)$$

Another form of linear filtering, non-linear filtering and/or normalisation may alternatively be applied at the pre-processing stage. For example, a low-pass filter may be used to reduce noise. Additionally or alternatively, a high-pass filter may be used to remove gradual image intensity changes such as lighting variations. A high-pass filter may also aid more consistent image normalisation. Normalisation is any method serving to reduce the variation between images of some parameter such as global mean brightness, global mean contrast or image histogram, or to reduce the variation across a single image of parameters such as local image brightness, local contrast or local histogram.

The processor 120 may, as in the present embodiment, generate the filtered image data in step S20 firstly by processing the received image data to generate lower spatial resolution image data defining a lower spatial resolution image of the vascular structure of the temporal vascular arcades of the retina. This may be done in any suitable way using techniques known to those skilled in the art, for example by appropriately sampling the received image data and (if necessary) applying any desired form of interpolation (e.g. bilinear interpolation), spatial anti-aliasing, etc. The processor 120 may reduce the spatial resolution of the received image data by a factor of 1.4 to 4, and more preferably 2 (as in the present embodiment). The processor 120 may then generate the filtered image data by filtering the generated lower spatial resolution image data so as to enhance linear structures in the image defined by the lower spatial resolution image data using, for example, the techniques described above.

Figure 3A:
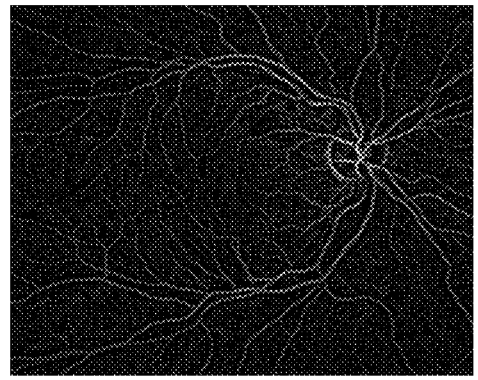
FIGS. 3A to 3C show results of filtering operations performed in step S20 in FIG. 2.
Figure 3B:
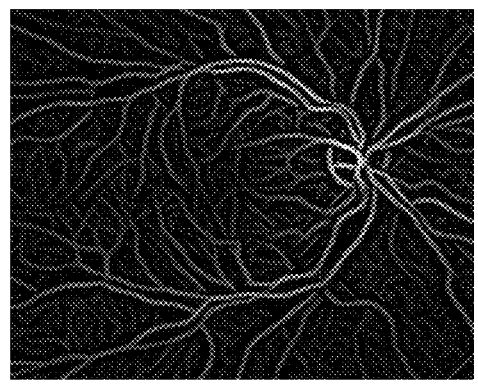
Figure 3C:
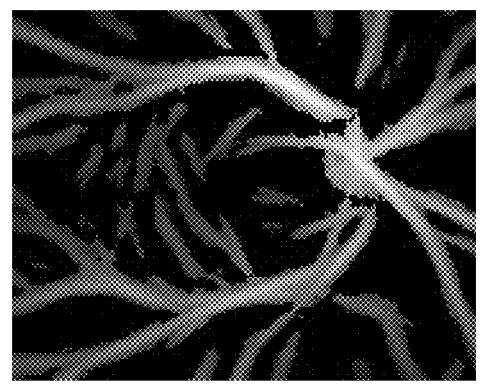

The processor 120 may then perform further processes of: (i) processing the filtered image data to generate lower spatial resolution filtered image data defining a low spatial resolution image of the vascular structure of the temporal vascular arcades of the retina (the spatial resolution again preferably being reduced by a factor of 1.4 to 4, more preferably 2); and (ii) filtering the lower spatial resolution filtered image data generated in process (i) so as to enhance linear structures in the image defined by the lower spatial resolution filtered image data, wherein the filtered image data processed in any repeat of the process (i) is the filtered image data generated in the preceding performance of process (ii). In this way, processes (i) and (ii) may be performed iteratively, two or more times (and preferably twice), with the output of process (ii) in one iteration serving as the input to process (i) in the next iteration. Examples of the initial image enhancement and two successive repeats of processes (i) and (ii) are shown in FIGS. 3A, 3B and 3C, respectively, in which the resulting smoothed images have been sized to the same dimensions.

The process then proceeds to step S30, wherein the processor 120 transforms the filtered image data generated at the end of the above-described processes in step S20 (or the received image data in embodiments where step S20 is omitted) such that the vascular structure in the image defined by the transformed image data is more circular than the vascular structure in the image defined by the filtered image data (or received image data, as the case may be). This transformation may be done by lowering the resolution of the filtered image data in either the horizontal or the vertical direction of the image by an amount required to make the vascular structure more circular in the image, using techniques known to those skilled in the art. Making the vascular structure in the image more circular allows the simplified processing operations described herein below to be used, rather than more complex and computationally expensive calculations that would be required to estimate the location of the fovea in an image wherein the vascular structure is elliptical.

In step S40 in FIG. 2, the processor 120 calculates, for each of a plurality of pixels $p_{ij}$ of the transformed image (where i and j represent the column and row of the pixel array, respectively), a respective local orientation vector indicative of the orientation of any blood vessel present in the image at or adjacent to the pixel (in other words, any blood vessel that may be present in the image at, or in the vicinity of (e.g. within a predetermined number of one or more pixels from), the pixel). Such a local orientation vector may be found in a number of different ways, using techniques known to those skilled in the art. Local orientation and edge strength can be evaluated using first-order or second-order derivatives of image intensity, for example. First-order derivatives can be calculated by convolution with a Sobel or other kernel (as discussed above). Local orientation is then the arc tangent of the ratio of the y-component and the x-component of the gradient. Second-order derivatives can be calculated by repeated convolution with a Sobel or other kernel. The local orientation is then the arc tangent of the y-component and the x-component of the eigenvector with the largest eigenvalue of the Hessian matrix:

$$\begin{bmatrix} \frac{d^2z}{dx^2} & \frac{d^2z}{dydx} \\ \frac{d^2z}{dxdy} & \frac{d^2z}{dy^2} \end{bmatrix},$$

where z is image intensity.

For example, the local orientation vector may be calculated by finding the eigenvector of the Hessian matrix at each pixel that has the largest eigenvalue. Alternatively, the local orientation vector may, as in the present embodiment, take the form of the pixel value gradient vector, which tends to have a large magnitude in the boundary region of a blood vessel in the retinal image, where the pixel values change relatively rapidly one pixel to the next in the direction perpendicular to the local orientation of the blood vessel segment (i.e. along or opposite to the flow direction of the blood vessel; in other words, the direction along which the blood vessel extends in the image), and is generally small away from the blood vessels. The pixel value gradient vector at a pixel in a region of the retinal image showing a part of a blood vessel (particularly an edge portion of the blood vessel) is thus indicative of the orientation of the blood vessel.

Thus in the present embodiment, the processor 120 calculates in step S40, for each of the plurality of pixels $p_{ij}$ of the transformed image data, a respective pixel value gradient vector g(i,j) (in other words, the gradient of image intensity) at the pixel. The pixels may be considered to hold respective values of a discrete function f(i,j) whose value varies with position (i,j) on the array of pixels, with the pixel value gradient vector g at any pixel pointing in the direction of greatest increase of the function at that pixel, the magnitude of the pixel value gradient vector, |g|, being the slope of the function in that direction. As noted above, in an image of a retina, the magnitude of the pixel value gradient vector will generally be highest at the edges of a blood vessel, where there is a rapid change in pixels values in the direction perpendicular to the direction along which the blood vessel extends.

Any well-known technique for calculating the pixel value gradient vector g may be used, for example as described in "Digital Image Processing" by R. C. Gonzalez and R. E. Woods (Pearson, Aug. 31, 2007) or "Digital Image Processing and Computer Vision" by R. J. Schalkoff (John Wiley & Sons, Sep. 2, 1992). Typical methods use Sobel, Prewitt or Roberts operators, which can be used to determine the gradient x- and y-components, the gradient magnitude and the gradient orientation. The plurality of pixels $p_{ij}$ at which the pixel value gradient vector g(i,j) is calculated in step S40 may encompass all of the pixels of the transformed image data, or only some of those pixels. The processor 120 may, for example, employ a mask defining one or more regions of the transformed image (e.g. a peripheral region of the image), in which region(s) no calculation of the pixel value gradient vector g is to be performed.

The process may, as in the present embodiment, then proceed to an optional step S50, wherein the processor 120 selects pixels $p^s_{ij}$ from the plurality of pixels $p_{ij}$ such that the magnitude of the local orientation vector (in this embodiment, the calculated pixel value gradient vector g(i,j)) at each of the selected pixels $p^s_{ij}$ exceeds a threshold. This optional step disqualifies pixels at which the local orientation vector (i.e. |g|) is small (i.e. pixels unlikely to be located within a blood vessel or at a blood vessel edge) from the further processing operations described below, thereby saving computational resources and, moreover, allowing the location of the fovea to be estimated with higher accuracy. The processor 120 may, for example, select the pixels $p^s_{ij}$ from the plurality of pixels $p_{ij}$ such that the magnitude of the calculated pixel value gradient vector g(i,j) at each of the selected pixels $p^s_{ij}$ exceeds a predetermined percentile of pixel value gradient vector magnitudes of the pixels $p_{ij}$. The predetermined percentile may be the $50^{th}$ percentile, or it may, as in the present embodiment, more preferably be the $80^{th}$ percentile.

Figure 4:
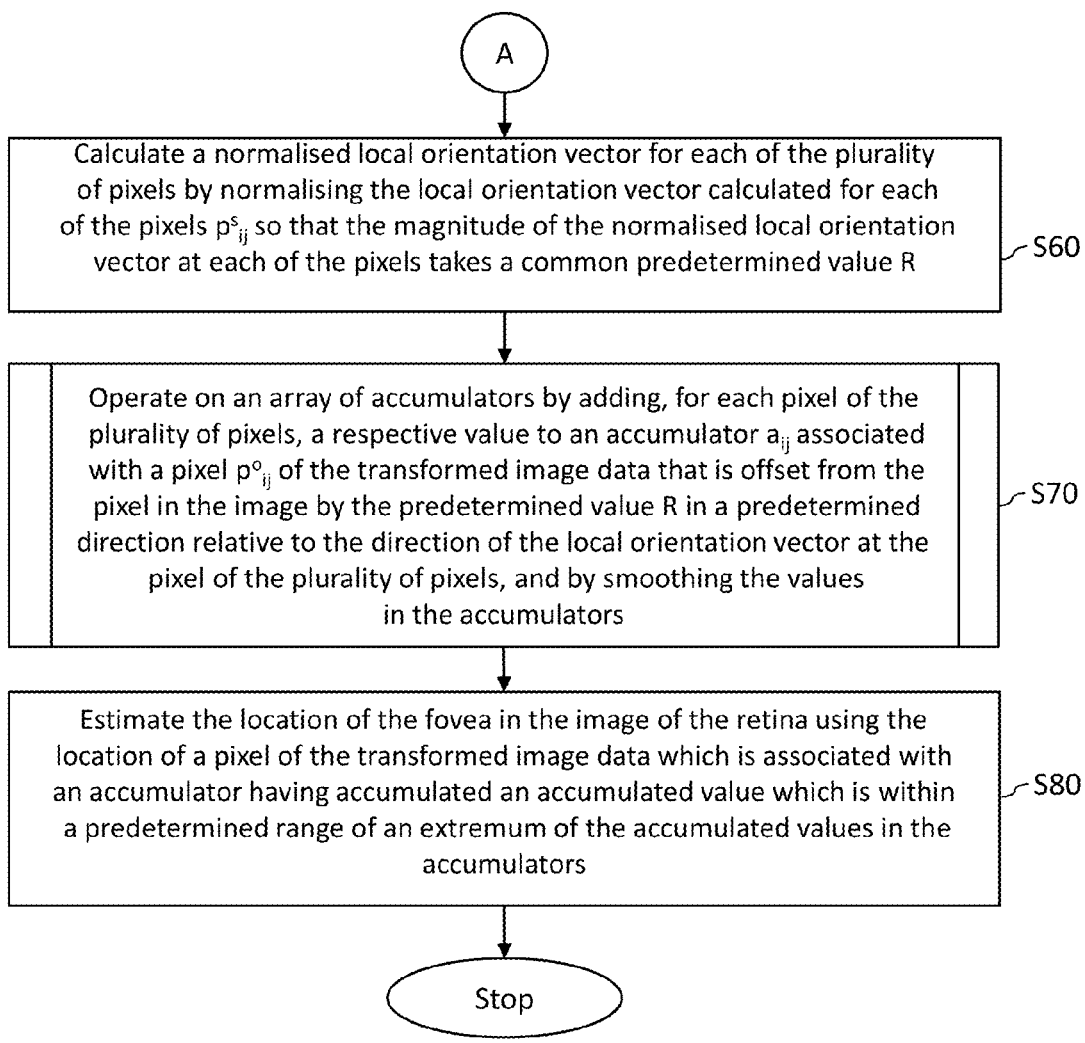
FIG. 4 is a continuation of the flow diagram in FIG. 2.

Proceeding to step S60 in FIG. 4, the processor 120 calculates a normalised local orientation vector for each of the selected pixels $p^s_{ij}$ by normalising the local orientation vector calculated for each of the selected pixels $p^s_{ij}$ so that the magnitude of the normalised local orientation vector at each of the selected pixels $p^s_{ij}$ takes a predetermined value that is the same for all of the selected pixels $p^s_{ij}$. Where step S50 is omitted, the processor 120 calculates in step S60 a normalised local orientation vector for each of the plurality of pixels $p_{ij}$ by normalising the local orientation vector calculated for each of the pixels $p_{ij}$ so that the magnitude of the normalised local orientation vector at each pixel takes a predetermined value that is the same for all of the pixels.

As the local orientation vector is, by way of example, the pixel value gradient vector in the present embodiment, the processor calculates in step S60 a normalised pixel value gradient vector g''(i,j) for each of the selected pixels $p^s_{ij}$ by normalising the pixel value gradient vector g(i,j) calculated for each of the selected pixels $p^s_{ij}$ so that the magnitude of the normalised pixel value gradient vector, |g''(i,j)|, at each of the selected pixels $p^s$ takes a predetermined value that is the same for all of the selected pixels $p^s_{ij}$. Thus, |g''(i,j)| is the same for all of the selected pixels $p^s_{ij}$, while the orientation of g'' will depend on the local pixel value gradient at each selected pixel $p^s_{ij}$ and will therefore generally differ between the selected pixels. The processor 120 preferably calculates the normalised pixel value gradient vector $g_n$ (or other form of local orientation vector, as noted above) for each of the selected pixels $p^s_{ij}$ so that the magnitude of said vector (i.e. R) at each of the selected pixels $p^s_{ij}$ is between 0.5 DFD and 1.3 DFD, where DFD is the distance between the fovea and the center of the optic disc in the received image of the retina (expressed in terms of a number of pixels, for example). The value of DFD may readily be determined (e.g. by inspecting an image of the retina), and subsequently used in the automatic processing of the same image or other images that have been obtained under similar conditions, using the techniques described herein. In other words, a suitable value of the unit DFD to be used for automatically processing a batch of retinal images may be determined by manually examining a set of training images which are representative of the images in the batch to obtain a suitable measure of DFD, which could then be used in the processing of the batch of images.

In process S70, the processor 120 performs operations described hereinafter using an array of accumulators. Each accumulator, $a_{ij}$, of the array is configured to receive real values (which may or may not be integers, and may be positive or negative) and calculate an accumulated value that is indicative of an accumulation of the received values. For example, each accumulator $a_{ij}$ may, as in the present embodiment, sum positive integer values (also referred to hereinafter as "votes") which it receives such that the accumulated value is a sum of the received values. Each accumulator $a_{ij}$ may add each received value to a sum of any previously received values calculated thereby (in other words, the accumulator $a_{ij}$ may update its accumulated value on receiving each new value), or it may temporarily store the received values before calculating their sum at the end of the operations in step S70. However, in other embodiments, each accumulator $a_{ij}$ may alternatively be initialised to store an initial value which is a sufficiently large positive number, and add subsequently received negative integer values to the stored value (or deduct received positive values from the stored value), thereby effectively decrementing the stored value with each value it receives. In this case, the accumulated value at the end of the operations in step S70 is also indicative of an accumulation of the received values.

In the present embodiment, the array of accumulators is implemented by the processor 120 executing the aforementioned instructions in the instruction store 140 to appropriately address and manage (including writing to, reading from and otherwise processing information stored in) storage elements in the working memory 130. Each accumulator $a_{ij}$ is associated with a respective pixel $p_{ij}$ of the received image data, for example by the processor 120 in the working memory 130 an association, link or pointer relating each accumulator $a_{ij}$ to a corresponding pixel $p_{ij}$ in the image data.

In step S70, the processor 120 operates on the array of accumulators by adding, for each pixel of the plurality of pixels, a respective value to an accumulator $a_{ij}$ associated with a pixel $p^o_{ij}$ of the transformed image data that is offset (i.e. separated by a displacement vector) from the pixel of the plurality of pixels by the predetermined value in a predetermined direction relative to the direction of the local orientation vector at the pixel of the plurality of pixels, and by smoothing the values in the accumulators $a_{ij}$. The process S70 will now be described in more detail with reference to FIGS. 5 and 6.

Figure 5:
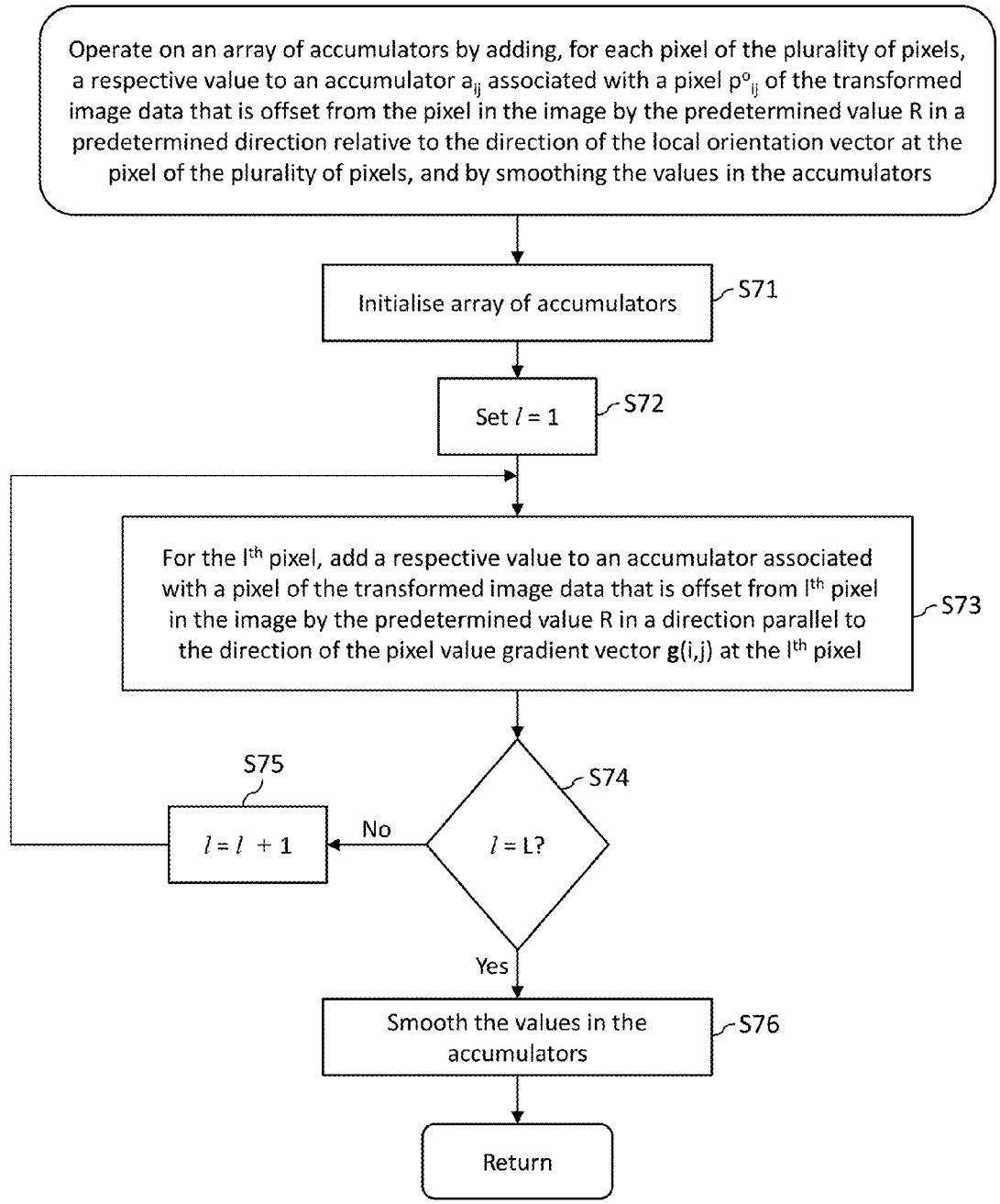
FIG. 5 is a flow diagram illustrating process S70 in FIG. 4.

Referring firstly to FIG. 5, in step S71, the processor initialises the array of accumulators so that the accumulated value stored in each accumulator $a_{ij}$ is common constant value; in this embodiment, zero. In the aforementioned alternative embodiments, where the accumulators subtract received positive values from (or, equivalently, add received negative values to) an initial (starting) value, each accumulator $a_{ij}$ is set to store the initial value in step S71.

In step S72, an index I, which is used to reference each of the selected pixels $p^s_{ij}$ in turn, is set to an initial value of 1.

Then, in step S73, the processor 120 processes a first of the selected pixels $p^s_{ij}$ (as I=1 at this stage) by adding a value (which, by way of example is 1 in the present embodiment) to an accumulator $a_{ij}$ of the accumulator array which is associated with a pixel $p^o_{ij}$ of the received image data that is offset (i.e. spaced apart) from the selected pixel $p^s_{ij}$ in the image data by the predetermined value R in a predetermined direction relative to the direction of the local orientation vector at the selected pixel. As the local orientation vector is the pixel value gradient vector $g(i,j)$ in this embodiment, the predetermined direction is parallel to direction of the pixel value gradient vector $g(i,j)$ at the selected pixel $p^s_{ij}$. In other embodiments, the predetermined direction may be perpendicular to the direction of the local orientation vector, or be at another predefined angle relative to the direction of the local orientation vector, depending on how the local orientation vector is calculated. The offset considered in step S73 will generally be in a direction perpendicular to the direction in which the blood vessel illustrated by the selected pixel extends at the selected pixel, as illustrated in FIG. 6.

Figure 6:
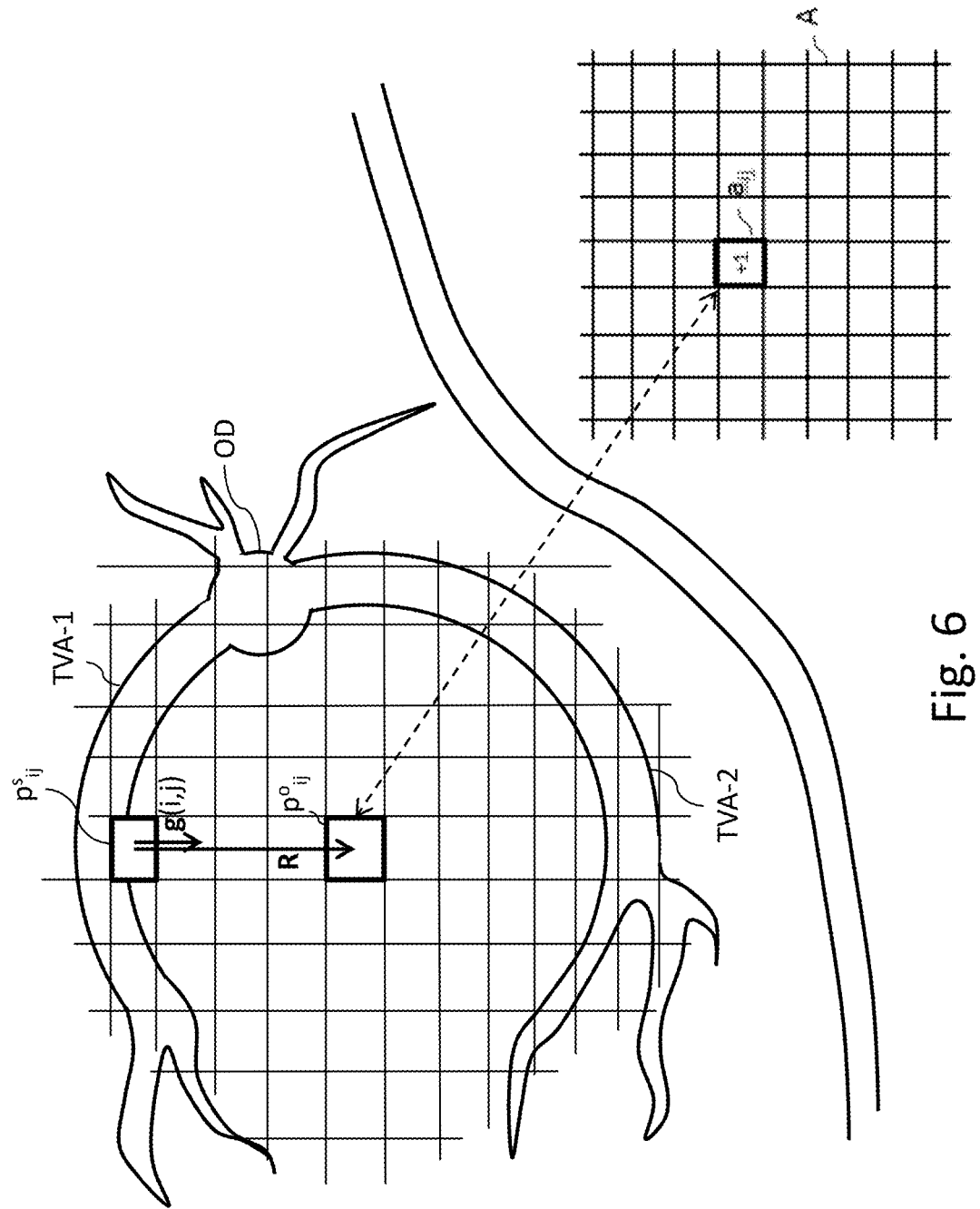
FIG. 6 is a schematic illustrating the relationship between pixels $p^s_{ij}$ and $p^o_{ij}$ of a retinal image and an accumulator $a_{ij}$ of an accumulator array described herein.

More particularly, FIG. 6 illustrates the relationship between pixels $p^s_{ij}$ and $p^o_{ij}$ of the retinal image data and an accumulator $a_{ij}$ of the accumulator array A. In FIG. 6, the transformed image data is illustrated in the upper part of the figure, and defines an image of a retina having an optic disc OD and temporal vascular arcades TVA-1 and TVA-2, which converge on the optic disc OD via respective paths that are substantially arcs of a circle centered on the fovea (not shown in FIG. 6) in the transformed image of the retina shown in FIG. 6. The lower part of FIG. 6 illustrates a part of the accumulator array A comprising the aforementioned accumulator $a_{ij}$. As illustrated in FIG. 6, pixel $p^o_{ij}$ is taken to be a pixel which lies on a line that is parallel to the direction of $g(i,j)$ at $p^s_{ij}$, and whose distance from $p^s_{ij}$ along that line is closest to R (in other words, the pixel to which a vector R points, where R is a vector displacement in the image plane from $p^s$ calculated such that $|R|=|g^n(i,j)|=R$ and $R \times g(i,j)=0$). The processor 120 determines which of the pixels in the transformed image data has the calculated offset R (rounded to the nearest pixel) in relation to the first selected pixel $p^s$ on the basis of the normalised pixel value gradient vector $g^n(i,j)$ calculated for the first selected pixel $p^s_{ij}$ in step S60. Unless the processor 120 employs a mask to exclude candidate locations for pixel $p^o_{ij}$, it may, as in the present embodiment, furthermore determine which of the pixels in the retinal image has an offset of −R (rounded to the nearest pixel) in relation to the first selected pixel $p^s_{ij}$, also on the basis of the normalised pixel value gradient vector $g^n(i,j)$ calculated for the first selected pixel $p^s_{ij}$ in step S60.

By the process in step S73, the processor 120 effectively registers a "vote" with each of two accumulators of the accumulator array A corresponding to respective pixels (at R and −R relative to $p^o_{ij}$) that are taken to be a candidates for the location of the fovea.

The process then proceeds to step S74, wherein the processor 120 determines whether the index I has reached the limit L, L being the number of pixels $p^s_{ij}$ having been selected in step S50. If the counter I has not yet reached the limit L, then the counter I is incremented by 1 in step S75, and the process loops back to step S73, where the next selected pixel $p^s_{ij}$ is processed as described above. In this way, each pixel in the image data at which the pixel value gradient magnitude exceeds the threshold contributes a vote in an accumulator corresponding to a pixel that is offset from the aforementioned pixel by a distance R, in a direction which is parallel to the local gradient and thus in a direction perpendicular to the local direction of the vascular structure.

Once all of the selected pixels $p^s_{ij}$ have been processed (I=L in step S74), the process proceeds to step S76, wherein the processor 120 smooths the accumulated values in the accumulators to generate a response map. After a large number of selected pixels have been processed, a higher number of votes will have been registered in accumulators associated with pixels in the transformed image that are located near the centre of the aforementioned circle (along whose arcs the temporal vascular arcades extend), and this will be reflected in the response map. The array of accumulated values may be smoothed by applying any image-smoothing (or low-pass filtering) operation to the array. Examples of suitable image-smoothing methods are described in "Digital Image Processing" by R. C. Gonzalez and R. E. Woods (Pearson, Aug. 31, 2007) and "Digital Image Processing and Computer Vision" by R. J. Schalkoff (John Wiley & Sons, Sep. 2, 1992). The smoothing operation can be a linear operation such as convolution by a kernel which could have, for instance, a Gaussian shape or an array of similar values (to make a moving-average filter). Smoothing or low-pass filtering can also be performed in the frequency domain. The smoothing operation could also be a non-linear operation such as a median filter or a morphological filter. The processor 120 may, as in the present embodiment, smooth the values in the accumulators using a Gaussian kernel which preferably has a standard deviation of 0.02 DFD to 0.5 DFD, and more preferably 0.075 DFD to 0.25 DFD, and yet more preferably 0.15 DFD. In any case, the response map is indicative of the probability distribution for the location of the fovea in the image of the retina.

Referring again to FIG. 4, after the completion of S70, the process proceeds to step S80, where the processor 120 estimates the location of the fovea in the image of the retina using the location of a pixel of the transformed image data which is associated with an accumulator of the array having accumulated an accumulated value which is a local or a global maximum among the accumulated values in the array of accumulators (the global maximum being the highest accumulated value of all the accumulators). The location of the fovea may be estimated as the location of the aforementioned pixel of the transformed image, or a pixel at the corresponding location in the received image (i.e. pre-transformation), or as the location of a pixel that is separated from either of these pixels by a predetermined displacement vector (determined, e.g. from experience or training). More generally, the processor 120 may estimate the location of the fovea using the location of a pixel in the received image data which is associated with an accumulator having accumulated an accumulated value that is within a predetermined range of values below a local or a global maximum among the accumulated values in the array of accumulators (the range, where it is non-zero, spanning, e.g. 5% or 10% of the maximum value). The locations of two or more local maxima determined from the response map may be used to estimate the location of the fovea. For example, multiple maxima may be chosen by taking all maxima which are above a certain threshold. Multiple maxima may be found, and a choice between which of these is associated with a pixel corresponding to the location of the fovea may be deferred to a subsequent data processing stage. A predetermined region of interest in the response map may be used to limit the choice of maxima. For example, the region of interest could be the region over which the fovea is known from experience to be very likely to occur.

In some embodiments (for example, where the accumulated values are negative or where the accumulators decrement an initially set count with each received "vote"), the processor 120 may estimate the location of the fovea in the retinal image as (or based on) the location of a pixel of the transformed image data which is associated with an accumulator of the array having accumulated an accumulated value which is a local or a global minimum among the accumulated values in the array of accumulators. Thus, the processor 120 may more generally determine the location of the fovea in the image of the retina using the location of a pixel of the transformed image data which is associated with an accumulator of the array having accumulated an accumulated value which is a (local or global) extremum of the accumulated values in the array of accumulators.

Embodiment 2

In the present embodiment, the processor 120 operates not on one but on N accumulator arrays, where $N \geq 2$. Each of these arrays of accumulators is associated with a respective one of N different quantised directions along which the pixel value gradient vector g may be oriented, and is labelled with a corresponding index n, where n=1, . . . N. The possible directions along which g may be oriented are taken to fall within the range of angles $[0, \pi]$, and this range is quantised into N sub-ranges or "quantised directions". For example, where N=4, any vector g(i,j) may be classified as being oriented along a first quantised direction corresponding to angular range $[0, \pi/4)$, a second quantised direction corresponding to angular range $[\pi/4, \pi/2)$, a third quantised direction corresponding to angular range $[\pi/2, 3\pi/4)$, or a fourth quantised direction corresponding to angular range $[3\pi/4, \pi]$. The function $\text{round}[N\text{mod}(\theta,\pi)/\pi-0.5]$, where $\theta = \arctan(g_y/g_x)$, $g_y$ is the y-component of g and $g_x$ is the x-component of g, may be used to quantise the direction of g. The accumulator array associated with the first quantised direction is assigned n=1, the accumulator array associated with the second quantised direction is assigned n=2, accumulator array associated with the third quantised direction is assigned n=3, and accumulator array associated with the fourth quantised direction is assigned n=4. In the present embodiment, an accumulator in the $i^{th}$ column and the $j^{th}$ row of the $n^{th}$ accumulator array (associated with the $n^{th}$ quantised direction) is denoted $a_{ijn}$. Each accumulator $a_{ijn}$ in each accumulator array is associated with a respective pixel in the retinal image data, so that there are N accumulators (one in each of the N accumulator arrays) associated with each pixel in the transformed image data.

Figure 7:
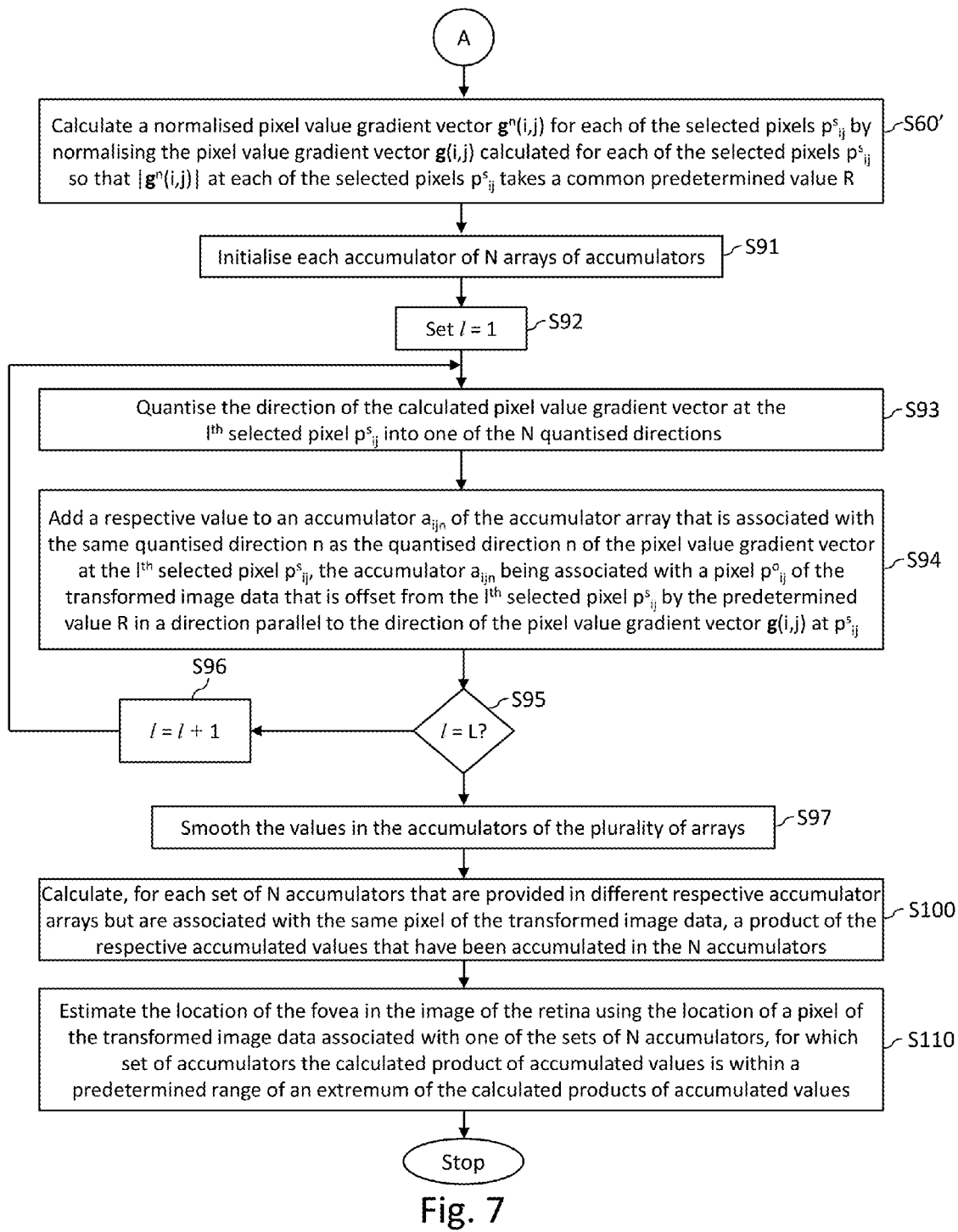
FIG. 7 is an alternative continuation of the flow diagram in FIG. 2, which illustrates a process by which the image-processing apparatus according to a second embodiment processes image data defining an image of a vascular structure of temporal vascular arcades of a retina to estimate a location of the fovea in the image.

FIG. 7 is a flow diagram illustrating the process by which the image-processing apparatus 170 of the present embodiment processes image data defining an image of a retina to determine the location of the fovea, which comprises steps S10 to S50 and the exemplary form of step S60 of the first embodiment described above (which is labelled S60' in FIG. 7), whose description will not be repeated here, as well as a sequence of operations performed on the N arrays of accumulators, which will now be described. It should be noted that the structure and operation of the present embodiment is the same as the first embodiment, apart from the differences hereinafter described. Furthermore, the possible modifications to the first embodiment mentioned above may also be made to the present embodiment.

In step S91, each accumulator of the N arrays of accumulators is initialised in the same way as in step S71 of FIG. 5, so that the accumulated value stored in each accumulator $a_{ij}$ is zero.

In step S92, an index I, which is used to reference each of the selected pixels $p^s_{ij}$ in turn, is set to an initial value of 1.

Then, in step S93, the processor 120 processes a first of the selected pixels $p^s_{ij}$ (as I=1 at this stage) by quantising the direction of either g(i,j) or g''(i,j) at the first selected pixel $p^s_{ij}$ into one of the N quantised directions. Thus, one of the values of n (from 1 to N) may be associated with the first selected pixel $p^s_{ij}$, depending on the direction of g at that pixel, and this allows the corresponding accumulator array (having the same value of n) to be identified and accessed.

In step S94, the processor 120 adds a constant value (e.g. 1, as in the first embodiment) to an accumulator $a_{ijn}$ of an accumulator array that is associated with the same quantised direction as the quantised direction of g(i,j) at the first selected pixel $p^s_{ij}$, wherein the accumulator to which the value is added is associated with a pixel $p^o_{ij}$ of the transformed image data that is (as in the first embodiment) offset from the first selected pixel $p^s_{ij}$ by the predetermined value R in a direction parallel to the direction of g(i,j) at the first selected pixel $p^s_{ij}$. Thus, in the present embodiment, which accumulator receives the "vote" for the selected pixel depends also on the direction of g(i,j) at the selected pixel, with the accumulator associated with the same quantised direction as the quantised direction of g(i,j), and which is associated with a pixel $p^o_{ij}$ of the received image data that is offset from the selected pixel by distance R in a direction parallel to the direction of g(i,j) at the selected pixel, receiving the vote.

The process then proceeds to step S95, wherein the processor 120 determined whether the index I has reached the limit L, L being the number of pixels $p^s_{ij}$ having been selected in step S50. If the counter I has not yet reached the limit L, then the counter I is incremented by 1 in step S96, and the process loops back to step S93, where the next selected pixel $p^s_{ij}$ is processed as described above. In this way, each selected pixel in the transformed image data at which |g| exceeds the threshold contributes a vote in an accumulator $a_{ijn}$ which is associated with the same quantised direction n as the quantised direction of g at the selected pixel, and which corresponds to a pixel that is offset from the selected pixel by a distance R, in a direction which is parallel to the local gradient at the selected pixel and thus in a direction normal to the local direction of the blood vessel at the selected pixel $p^s_{ij}$.

Once all of the selected pixels $p^s_{ij}$ have been processed (I=L in step S95), the process proceeds to step S97, wherein the processor 120 smooths the accumulated values in the plurality of arrays of accumulators. The smoothing operation may be performed on accumulated values within one or more of the arrays, using the techniques described in connection with the first embodiment. Thus, Gaussian blurring of one or more accumulator arrays may be performed. Additionally or alternatively, the smoothing operation may be performed on values accumulated in the N accumulators $a_{ijn}$ having the same indices i and j but different indices n (from 1 to N), using the same techniques.

In step S100, the processor 120 calculates, for each set of N accumulators $a_{ijn}$ that are provided in different respective accumulator arrays and associated with the same pixel $p^o_{ij}$ of the transformed image data, a product of the respective accumulated values that have been accumulated in the N accumulators $a_{ijn}$. The product is effectively a "soft AND" operation across the different gradient orientations, so that the pixels in the image associated with high values of this product tend to be at locations about which blood vessels circle in the transformed image of the retina. In other words, wherever this product is non-zero, there may likely have been a contribution from each of the N directions associated with the N accumulator arrays.

The number of arrays of accumulators, N, is preferably such that 2≤N≤32, and more preferably 4≤N≤16. If N=1 (as in the first embodiment) then the method is simplified in that there is no need to quantise the gradient orientation and there is no need for the "soft AND" combination of accumulator arrays. However, this simplification comes at a cost of a decrease in "signal-to-noise ratio" by a factor of 2 as compared to the case where N=8, for example. Using values of N that are too high, on the other hand, increase the computational cost and may not allow the location of the optic disc or other anatomical feature to be determined reliably, as the product calculated in step S100 may be zero for all pixel locations. For the detection of the optic disc, it is preferable that N=8. For the detection of vessel junctions, a smaller value of N may be used, for example 3 or 4.

The process proceeds from step S100 to step S110, wherein the processor 120 estimates the location of fovea in the image of the retina using the location of a pixel of the transformed image that is associated with a set of N accumulators, for which set the calculated product of accumulated values is a local or a global maximum among the calculated products of accumulated values. The location of the fovea may be estimated as the location of the aforementioned pixel of the transformed image, or a pixel at the corresponding location in the received image (i.e. pre-transformation), or as the location of a pixel that is offset in relation to either of these pixels by a predetermined amount (determined, e.g. from experience or training). More generally, the processor 120 may estimate the location of the fovea using the location of a pixel of the transformed image data that is associated with a set of N accumulators, for which set the calculated product of accumulated values is within a predetermined range of values below a (local or global) maximum among the calculated products of accumulated values. The locations of two or more local maxima determined from the response map may be used to estimate the location of the fovea. For example, multiple maxima may be chosen by taking all maxima which are above a certain threshold. Multiple maxima may be found, and a choice between which of these is associated with a pixel corresponding to the location of the fovea may be deferred. A predetermined region of interest in the response map may be used to limit the choice of maxima. For example, the region of interest could be the region over which the fovea is known from experience to be very likely to occur.

[Modifications and Variations]

Many further modifications and variations can be made to the embodiments described above.

Figure 8:
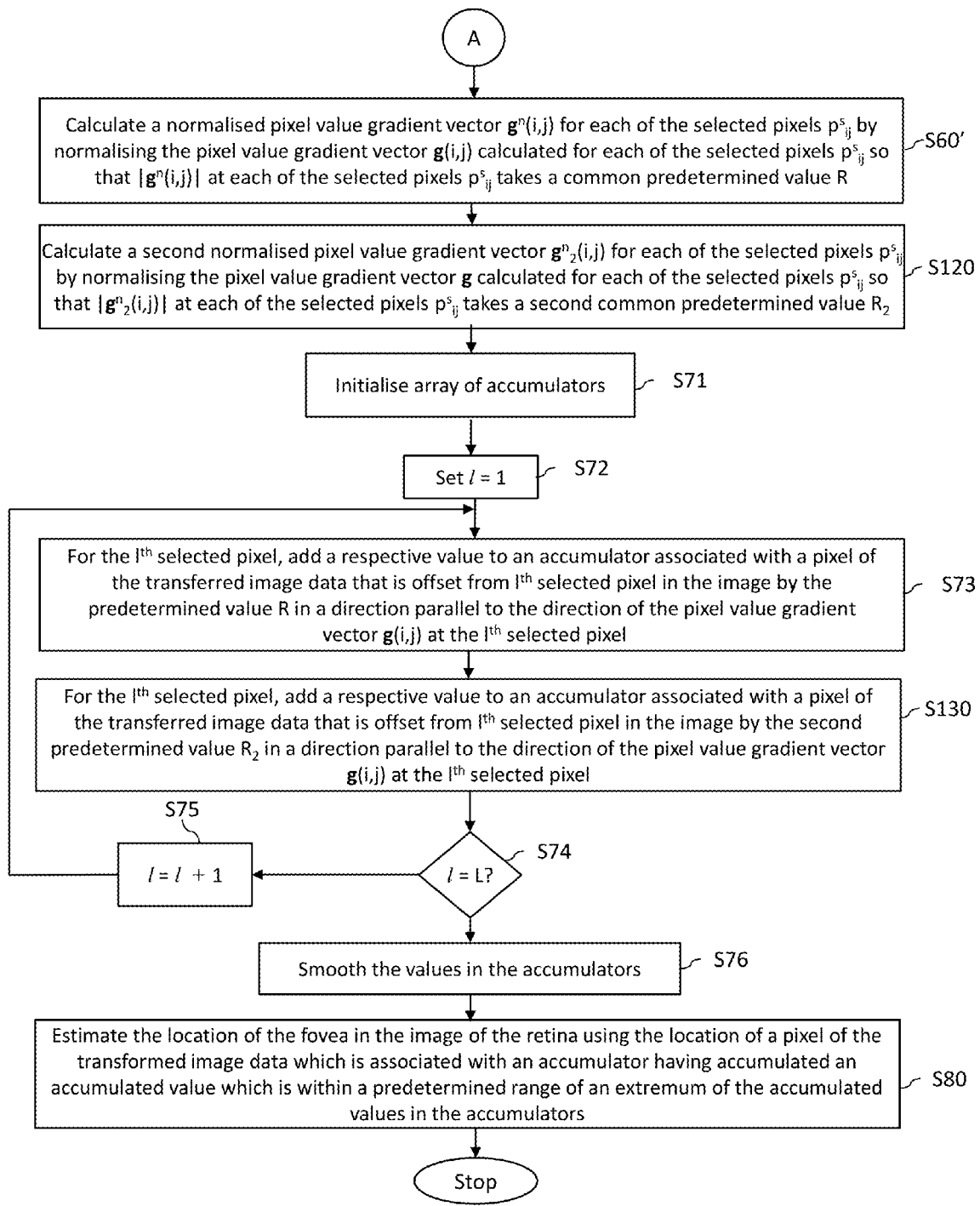
FIG. 8 is another alternative continuation of the flow diagram in FIG. 2, which illustrates a process by which the image-processing apparatus according to a variant of the first embodiment processes image data defining an image of a vascular structure of temporal vascular arcades of a retina to estimate a location of the fovea in the image.

For example, the first embodiment described above with reference to FIGS. 2 to 6 may, as illustrated in FIG. 8, be modified to include an additional step after step S60' and before step S72, namely an additional step S120, wherein the processor 120 calculates a second normalised pixel value gradient vector $g''_2(i,j)$ for each of the selected pixels $p^s_{ij}$ by normalising the pixel value gradient vector g calculated for each of the selected pixels $p^s_{ij}$ so that $|g''_2(i,j)|$ at each of the selected pixels $p^s_{ij}$ takes a second common predetermined value $R_2$. The first embodiment may, as also illustrated in FIG. 8, be further modified to include an additional step S130 that is performed for each value of index I, wherein the processor 120 adds, for the $I^{th}$ selected pixel, a respective value to the accumulator which is associated with a pixel in the transformed image data that is offset from the $I^{th}$ selected pixel by the second predetermined value $R_2$ in the direction parallel to the direction of the pixel value gradient vector g at the $I^{th}$ selected pixel. In other respects, this variant is the same as the first embodiment. The addition in step S130 may alternatively be made to a second accumulator layer that is associated with the second predetermined value $R_2$, with the corresponding elements in the two accumulator arrays being combined after step S74, by some hard or soft OR operation such as element-by-element addition.

More generally, more than two normalised pixel value gradient vectors may be calculated prior to step S72, preferably each having a magnitude within the preferred ranges of $|g''(i,j)|$ set out above. In these cases, the values may be accumulated in a single accumulator array, or in a corresponding number of accumulator arrays before being combined in the manner set out above. Using more than one calculated normalised pixel value gradient vector in the process may allow the location of the fovea to be determined more reliably.

The above-described modifications may also be made to the second embodiment described above.

As a further modification, which may be made to either of the above-described embodiments, or combined with any of the above-described modifications to these embodiments, the selection of pixels in step S50 may be omitted so that the processor 120 calculates, each of a plurality of pixels $p_{ij}$ of the transformed (and optically pre-processed) image data, a respective pixel value gradient vector $g(i,j)$ at the pixel. In this variant, the processor 120 would then calculate $g''(i,j)$ for each of the plurality of pixels $p_{ij}$ by normalising the pixel value gradient vector calculated for each of the pixels $p_{ij}$ so that the $|g''(i,j)|$ at each of the pixels takes a common predetermined value R. The processor 120 would operate on the array of accumulators by adding, for each of the plurality of pixels $p_{ij}$, a respective value to an accumulator associated with a pixel $p^o_{ij}$ of the transformed image data that is offset from the pixel of the plurality of pixels $p_{ij}$ by the predetermined value R in a direction parallel to the direction of $g(i,j)$ at the pixel of the plurality of pixels, and smoothing the values in the accumulators. In this variant, the processor may add, as the respective value, a respective weighting to the accumulator associated with the pixel $p^o_{ij}$, the weighting being indicative of the magnitude of $g(i,j)$ at the pixel of the plurality of pixels. The processor would then estimate the location of the fovea in the image of the retina using the location of a pixel of the transformed image data which is associated with an accumulator having accumulated an accumulated value which is within a predetermined range of an extremum of the accumulated values in the accumulators, as described in more detail above. In this variant, there is a contribution from each of the plurality of pixels to the accumulator, although the size of this contribution from each pixel will depend on the magnitude of g(i,j) at that pixel.

Furthermore, the ordering of some of the method steps in the embodiments and modifications thereof described above may be varied. For example, the ordering of step S60' and S120, and similarly S73 and S130, in FIG. 8 may be reversed, or these steps may be performed in parallel. Furthermore, the initialisation of accumulator array A may be performed at any point in the process before step S73 in the process illustrated in FIG. 5, at any point in the process before step S93 in the process illustrated in FIG. 7, and at any point before step S73 (step S130, where the order of S73 and S130 is reversed) in the process illustrated in FIG. 8 (the initialisation of course being outside the loop over index I).

The invention claimed is:

1. A non-transitory computer-readable storage medium storing computer program instructions which, when executed by a processor, cause the processor to process image data defining an image of a vascular structure of temporal vascular arcades of a retina to estimate a location of a fovea of the retina in the image by:
   receiving the image data;
   transforming the received image data such that the vascular structure in the image defined by the transformed image data is more circular than the vascular structure in the image defined by the received image data;
   calculating, for each pixel of a plurality of pixels of the transformed image data, a respective local orientation vector indicative of an orientation of any blood vessel present in the image at or adjacent to the pixel;
   calculating a normalised local orientation vector for each pixel of the plurality of pixels by normalising the local orientation vector calculated for pixel of the plurality of pixels so that a magnitude of the normalised local orientation vector at each pixel of the plurality of pixels takes a common predetermined value;
   operating on an array of accumulators, wherein each accumulator in the array is associated with a respective pixel of the transformed image data, by:
      for each pixel of the plurality of pixels, adding a respective value to an accumulator associated with a pixel of the transformed image data that is offset from the pixel of the plurality of pixels by the predetermined value in a predetermined direction relative to a direction of the local orientation vector at the pixel of the plurality of pixels; and
      smoothing the values in the accumulators; and
   estimating the location of the fovea in the image of the retina using a location of a pixel of the transformed image data which is associated with a respective accumulator having accumulated an accumulated value which is within a predetermined range of an extremum of the accumulated values in the accumulators.

2. The non-transitory computer-readable storage medium according to claim 1, wherein the instructions, when executed by the processor, cause the processor to perform, prior to transforming the received image data, further processes of:
   (i) processing the received image data to generate lower spatial resolution image data defining a lower spatial resolution image of the vascular structure of the temporal vascular arcades of the retina;
   (ii) generating filtered image data by filtering the lower spatial resolution image data so as to enhance linear structures in the image defined by the lower spatial resolution image data,
   wherein the processor transforms the filtered image data such that the vascular structure in the image defined by the transformed image data is more circular than the vascular structure in the image defined by the filtered image data.

3. The non-transitory computer-readable storage medium according to claim 2, wherein the instructions, when executed by the processor, cause the processor to perform, at least once, prior to transforming the received image data, further processes of:
   (iii) processing the filtered image data to generate lower spatial resolution filtered image data defining a low spatial resolution image of the vascular structure of the temporal vascular arcades of the retina;
   (iv) filtering the lower spatial resolution filtered image data so as to enhance linear structures in the image defined by the lower spatial resolution filtered image data,
   wherein the filtered image data processed in any repeat of the process (iii) is the filtered image data generated in the preceding performance of process (iv), and
   wherein the filtered image data transformed by the processor is the filtered image data generated in the final performance of process (iv).

4. The non-transitory computer-readable storage medium according to claim 3, wherein the instructions, when executed by the processor, cause the processor to downsize the received image data by a factor of 1.4 to 4 in the performance of process (i), and to downsize the filtered image data by a factor of 1.4 to 4 in each performance of process (iii).

5. The non-transitory computer-readable storage medium according to claim 1, wherein the instructions, when executed by the processor, cause the processor to operate on a plurality, N, of arrays of accumulators, where N is an integer equal to at least 2, and wherein:
   each of the arrays of accumulators is associated with a respective one of N quantised directions for the local orientation vector;
   each of the accumulators in each of the N arrays is associated with a respective pixel in the transformed image data;
   the processor operates on the plurality of arrays of accumulators by:
      for each pixel of the plurality of pixels:
         quantising the direction of the calculated local orientation vector at the pixel into one of the N quantised directions; and
         adding a respective value to an accumulator of an accumulator array that is associated with the same quantised direction as the quantised direction of the local orientation vector at the pixel, the accumulator being associated with a pixel of the transformed image data that is offset from the pixel of the plurality of pixels by the predetermined value in the predetermined direction relative to the direction of the local orientation vector at the pixel of the plurality of pixels; and smoothing the values in the accumulators of the plurality of arrays;

the processor further calculates, for each set of N accumulators that are provided in different respective accumulator arrays and associated with the same pixel of the transformed image data, a product of the respective accumulated values that have been accumulated in the N accumulators; and the processor estimates the location of the fovea in the image of the retina using the location of a pixel of the transformed image data associated with at a set of N accumulators, for which set the calculated product of accumulated values is within a predetermined range of an extremum of the calculated products of accumulated values.

6. The non-transitory computer-readable storage medium according to claim 5, wherein N is an integer that is greater than or equal to 2 and less than or equal to 32.

7. The non-transitory computer-readable storage medium according to claim 1, wherein the instructions, when executed by the processor, further cause the processor to calculate a second normalised local orientation vector for each of the plurality of pixels by normalising the local orientation vector calculated for each of the plurality of pixels so that the magnitude of the second normalised local orientation vector at each of the pixels takes a second common predetermined value, and to further operate on the array of accumulators by:

for each pixel of the plurality of pixels, adding a respective value to an accumulator associated with a pixel in the transformed image data that is offset from the pixel of the plurality of pixels by the second predetermined value in the predetermined direction relative to the direction of the pixel value gradient vector at the pixel of the plurality of pixels.

8. The non-transitory computer-readable storage medium according to claim 1, wherein the instructions, when executed by the processor, cause the processor to process the image data defining the image of the vascular structure to estimate a location of the fovea of the retina in the image by performing a further process of:

selecting pixels from the plurality of pixels such that the magnitude of the calculated local orientation vector at each of the selected pixels exceeds a threshold, and by:

calculating the normalised local orientation vector for each of the selected pixels by normalising the local orientation vector calculated for each of the selected pixels so that the magnitude of the normalised local orientation vector at each of the selected pixels takes a common predetermined value; and operating on the array of accumulators by:

for each selected pixel of the selected pixels, adding a respective value to an accumulator associated with a pixel of the transformed image data that is offset from the selected pixel in the image by the predetermined value in the predetermined direction relative to the direction of the local orientation vector at the selected pixel.

9. The non-transitory computer-readable storage medium according to claim 8, wherein the instructions, when executed by the processor, cause the processor to select the pixels from the plurality of pixels such that the magnitude of the calculated local orientation vector at each of the selected pixels exceeds the $50^{th}$ percentile of local orientation vector magnitudes of the pixels in the transformed image data.

10. The non-transitory computer-readable storage medium according to claim 1, wherein the instructions, when executed by the processor, cause the processor to operate on each array of accumulators by:

for each pixel of the plurality of pixels of the transformed image data, adding, as the respective value, a respective weighting to the accumulator associated with a pixel in the transformed image data that is offset from the pixel of the plurality of pixels by the predetermined value in the predetermined direction relative to the direction of the local orientation vector at the pixel of the plurality of pixels, the weighting being indicative of the magnitude of the local orientation vector at the pixel of the plurality of pixels.

11. The non-transitory computer-readable storage medium according to claim 1, wherein the instructions, when executed by the processor, cause the processor to calculate the normalised local orientation vector for each pixel of the plurality of pixels so that that the magnitude of the normalised local orientation vector at each pixel of the plurality of pixels is between 0.5 DFD and 1.3 DFD, where DFD is a distance between the fovea and a center of an optic disc in the image defined by the received image data.

12. The non-transitory computer-readable storage medium according to claim 1, wherein the instructions, when executed by the processor, cause the processor to smooth the values in the accumulators using a kernel having a standard deviation of 0.02 DFD to 0.5 DFD, where DFD is a distance between the fovea and a center of an optic disc in the image defined by the received image data.

13. An image-processing apparatus comprising a processor and a memory, the memory storing instructions executable by the processor, which when executed by the processor cause the processor to process image data defining an image of a vascular structure of temporal vascular arcades of a retina to estimate a location of a fovea of the retina in the image by:

receiving the image data;

transforming the received image data such that the vascular structure in the image defined by the transformed image data is more circular than the vascular structure in the image defined by the received image data;

calculating, for each pixel of a plurality of pixels of the transformed image data, a respective local orientation vector indicative of an orientation of any blood vessel present in the image at or adjacent to the pixel;

calculating a normalised local orientation vector for each pixel of the plurality of pixels by normalising the local orientation vector calculated for each pixel of the plurality of pixels so that a magnitude of the normalised local orientation vector at each pixel of the plurality of pixels takes a common predetermined value;

operating on an array of accumulators, wherein each accumulator in the array is associated with a respective pixel of the transformed image data, by:

for each pixel of the plurality of pixels, adding a respective value to an accumulator associated with a pixel of the transformed image data that is offset from the pixel of the plurality of pixels by the predetermined value in a predetermined direction relative to a direction of the local orientation vector at the pixel of the plurality of pixels; and smoothing the values in the accumulators; and estimating the location of the fovea in the image of the retina using a location of a pixel of the transformed image data which is associated with a respective accumulator having accumulated an accumulated value which is within a predetermined range of an extremum of the accumulated values in the accumulators.

14. The image-processing apparatus according to claim 13, wherein the instructions, when executed by the processor, cause the processor to perform, prior to transforming the received image data, further processes of:
(i) processing the received image data to generate lower spatial resolution image data defining a lower spatial resolution image of the vascular structure of the temporal vascular arcades of the retina;
(ii) generating filtered image data by filtering the lower spatial resolution image data so as to enhance linear structures in the image defined by the lower spatial resolution image data,
wherein the processor transforms the filtered image data such that the vascular structure in the image defined by the transformed image data is more circular than the vascular structure in the image defined by the received image data.

15. The image-processing apparatus according to claim 14, wherein the instructions, when executed by the processor, cause the processor to perform, at least once, prior to transforming the received image data, further processes of:
(iii) processing the filtered image data to generate lower spatial resolution filtered image data defining a low spatial resolution image of the vascular structure of the temporal vascular arcades of the retina;
(iv) filtering the lower spatial resolution filtered image data so as to enhance linear structures in the image defined by the lower spatial resolution filtered image data,
wherein the filtered image data processed in any repeat of the process (iii) is the filtered image data generated in the preceding performance of process (iv), and
wherein the filtered image data transformed by the processor is the filtered image data generated in the final performance of process (iv).

16. The image-processing apparatus according to claim 15, wherein the instructions, when executed by the processor, cause the processor to downsize the received image data by a factor of 1.4 to 4 in the performance of process (i), and to downsize the filtered image data by a factor of 1.4 to 4 in each performance of process (iii).

17. The image-processing apparatus according to claim 13, wherein the instructions, when executed by the processor, cause the processor to operate on a plurality, N, of arrays of accumulators, where N is an integer equal to at least 2, and wherein:
each of the arrays of accumulators is associated with a respective one of N quantised directions for the local orientation vector;
each of the accumulators in each of the N arrays is associated with a respective one of the pixels in the transformed image data;
the instructions, when executed by the processor, cause the processor to:
operate on the plurality of arrays of accumulators by:
for each pixel of the plurality of pixels:
quantising the direction of the calculated local orientation vector at the pixel into one of the N quantised directions; and
adding a respective value to an accumulator of an accumulator array that is associated with the same quantised direction as the quantised direction of the pixel value gradient vector at the pixel, the accumulator being associated with a pixel of the transformed image data that is offset from the pixel of the plurality of pixels by the predetermined value in the predetermined direction relative to the direction of the local orientation vector at the pixel of the plurality of pixels; and
smoothing the values in the accumulators of the plurality of arrays;
further calculate, for each set of N accumulators that are provided in different respective accumulator arrays but are associated with the same pixel of the transformed image data, a product of the respective accumulated values that have been accumulated in the N accumulators; and
estimate the location of the fovea in the image of the retina using the location of a pixel of the transformed image data associated with one of the sets of N accumulators, for which set of accumulators the calculated product of accumulated values is within a predetermined range of an extremum of the calculated products of accumulated values.

18. The image-processing apparatus according to claim 17, wherein N is an integer that is greater than or equal to 2 and less than or equal to 32.

19. The image-processing apparatus according to claim 13, wherein the instructions, when executed by the processor, further cause the processor to calculate a second normalised local orientation vector for each of the plurality of pixels by normalising the local orientation vector calculated for each of the plurality of pixels so that the magnitude of the second normalised local orientation vector at each of the pixels takes a second common predetermined value, and to further operate on the array of accumulators by:
for each pixel of the plurality of pixels, adding a respective value to an accumulator associated with a pixel in the transformed image data that is offset from the pixel of the plurality of pixels by the second predetermined value in the predetermined direction relative to the direction of the local orientation vector at the pixel of the plurality of pixels.

20. The image-processing apparatus according to claim 13, wherein the instructions, when executed by the processor, cause the processor to process the image data to estimate the location of the fovea of the retina in the image by performing a further process of:
selecting pixels from the plurality of pixels of the transformed image data such that the magnitude of the calculated local orientation vector at each of the selected pixels exceeds a threshold, and by:
calculating the normalised local orientation vector for each of the selected pixels by normalising the local orientation vector calculated for each of the selected pixels so that the magnitude of the normalised local orientation vector at each of the selected pixels takes a common predetermined value; and
operating on the array of accumulators by:
for each selected pixel of the selected pixels, adding a respective value to an accumulator associated with a pixel of the transformed image data that is offset from the selected pixel in the image by the predetermined value in the predetermined direction relative to the direction of the local orientation vector at the selected pixel.

21. The image-processing apparatus according to claim 20, wherein the instructions, when executed by the processor, cause the processor to select the pixels from the plurality of pixels such that the magnitude of the calculated local orientation vector at each of the selected pixels exceeds the $50^{th}$ percentile of local orientation vector magnitudes of the pixels in the image.

22. The image-processing apparatus according to claim 13, wherein the instructions, when executed by the processor, cause the processor to operate on each array of accumulators by:
for each pixel of the plurality of pixels, adding, as the respective value, a respective weighting to the accumulator associated with a pixel in the transformed image data that is offset from the pixel of the plurality of pixels by the predetermined value in the predetermined direction relative to the direction of the local orientation vector at the pixel of the plurality of pixels, the weighting being indicative of the magnitude of the local orientation vector at the pixel of the plurality of pixels.

23. The image-processing apparatus according to claim 13, wherein the instructions, when executed by the processor, cause the processor to calculate the normalised local orientation vector for each pixel of the plurality of pixels so that that the magnitude of the normalised local orientation vector at each pixel of the plurality of pixels is between 0.5 DFD and 1.3 DFD, where DFD is the distance between the fovea and a center of an optic disc in the image defined by the received image data.

24. The image-processing apparatus according to claim 13, wherein the instructions, when executed by the processor, cause the processor to smooth the values in the accumulators using a kernel having a standard deviation of 0.02 DFD to 0.5 DFD, where DFD is a distance between the fovea and a center of an optic disc in the image defined by the received image data.

* * * * *